(12) United States Patent
Johnson et al.

(10) Patent No.: US 8,433,409 B2
(45) Date of Patent: Apr. 30, 2013

(54) IMPLANTABLE MEDICAL DEVICE BATTERY

(75) Inventors: David M. Johnson, Ham Lake, MN (US); Terrence J. Snyder, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 550 days.

(21) Appl. No.: 12/696,890

(22) Filed: Jan. 29, 2010

(65) Prior Publication Data

US 2011/0190842 A1 Aug. 4, 2011

(51) Int. Cl.
*A61N 1/05* (2006.01)
(52) U.S. Cl.
USPC .............. 607/36; 607/48; 607/37; 607/9
(58) Field of Classification Search .......... 607/36, 607/9
See application file for complete search history.

(56) References Cited

U.S. PATENT DOCUMENTS

| | | | |
|---|---|---|---|
| 4,035,909 A | 7/1977 | Dey | |
| 4,376,811 A | 3/1983 | Goebel | |
| 4,731,305 A | 3/1988 | Goebel et al. | |
| 5,273,203 A | 12/1993 | Webster | |
| 5,306,581 A | 4/1994 | Taylor et al. | |
| 5,776,632 A | 7/1998 | Honegger | |
| 6,111,198 A | 8/2000 | Tower | |
| 6,238,813 B1 * | 5/2001 | Maile et al. | 429/9 |
| 6,498,951 B1 * | 12/2002 | Larson et al. | 607/36 |
| 6,607,843 B2 | 8/2003 | Ruth, II et al. | |
| 6,721,604 B1 | 4/2004 | Robinson et al. | |
| 6,855,456 B2 | 2/2005 | Taylor et al. | |
| 7,070,881 B2 | 7/2006 | Kishiyama et al. | |
| 7,128,765 B2 | 10/2006 | Paulot et al. | |
| 7,291,186 B2 | 11/2007 | Zhang | |
| 7,410,512 B2 | 8/2008 | Tsukamoto et al. | |
| 2001/0002300 A1 | 5/2001 | Tinker et al. | |
| 2003/0083715 A1 | 5/2003 | Taylor et al. | |
| 2004/0101746 A1 | 5/2004 | Ota et al. | |
| 2004/0185337 A1 | 9/2004 | Ishizaki | |
| 2004/0191621 A1 | 9/2004 | Heller, Jr. | |
| 2004/0249431 A1 | 12/2004 | Ransbury et al. | |
| 2005/0021108 A1 * | 1/2005 | Klosterman et al. | 607/48 |
| 2006/0057458 A1 | 3/2006 | O'Dea et al. | |
| 2006/0085971 A1 | 4/2006 | Andrews et al. | |
| 2006/0136004 A1 * | 6/2006 | Cowan et al. | 607/33 |
| 2006/0178708 A1 | 8/2006 | Rorvick et al. | |

(Continued)

OTHER PUBLICATIONS

Reply to Written Opinion dated May 16, 2011, of international application No. PCT/US2011/022729, filed on Nov. 29, 2011, 12 pp.

(Continued)

*Primary Examiner* — Christopher D Koharski
*Assistant Examiner* — Michael Carey

(57) ABSTRACT

A battery comprises a tubular housing. An external surface of the tubular housing comprises a biocompatible material. The battery further comprises a battery header secured to an open end of the tubular housing, and the tubular housing and the battery header combine to form a substantially sealed enclosure. The battery also comprises one or more voltaic cells within the substantially sealed enclosure, and a feedthrough electrically connected to the voltaic cells and extending through the battery header to form a battery terminal. The battery header includes a radial groove opposite the tubular housing, and the radial groove is configured to receive a mating snap-fit electronic component subassembly of an implantable medical device.

20 Claims, 7 Drawing Sheets

U.S. PATENT DOCUMENTS

| | | |
|---|---|---|
| 2006/0222942 A1 | 10/2006 | Zhao et al. |
| 2006/0275659 A1 | 12/2006 | Kim et al. |
| 2007/0150020 A1 | 6/2007 | Hokanson et al. |
| 2007/0154801 A1 | 7/2007 | Hyung et al. |
| 2007/0179552 A1 | 8/2007 | Dennis et al. |
| 2007/0233195 A1 | 10/2007 | Wahlstrand et al. |
| 2007/0247786 A1 | 10/2007 | Aamodt et al. |
| 2008/0046059 A1 | 2/2008 | Zarembo et al. |
| 2008/0148554 A1 | 6/2008 | Merrill et al. |
| 2009/0112272 A1 | 4/2009 | Schleicher et al. |
| 2009/0321107 A1 | 12/2009 | Taylor et al. |
| 2010/0100164 A1 | 4/2010 | Johnson et al. |
| 2010/0305629 A1 | 12/2010 | Lund et al. |

OTHER PUBLICATIONS

U.S. Appl. No. 61/368,437, by Saul E. Greenhut, filed Jul. 28, 2010.
U.S. Appl. No. 13/096,881, by Vladimir Grubac, filed Apr. 28, 2011.
U.S. Appl. No. 13/074,948, by Nathan T. Lee, filed Mar. 29, 2011.
U.S. Appl. No. 13/104,715, by Sandeep Saurkar, filed May 10, 2011.
TexLoc Catalog 4155, "Fluoropolymer Extrusions Electrical Insulation Products", 22 pages. (last printed Apr. 15, 2011) http://www.texloc.com/Support/CAT-4155.
Professional Plastics, Tefzel ETFE Material Data Sheet, 2 pages. (last printed Apr. 15, 2011) http://www.professionalplastics.com/cgi-bin.
U.S. Appl. No. 12/547,875 by Jeffrey S. Lund et al., filed Aug. 26, 2009.
U.S. Appl. No. 12/548,234 by Jeffrey S. Lund et al., filed Aug. 26, 2009.
International Search Report and Written Opinion of international application No. PCT/US2011/022729, dated May 16, 2011, 13 pp.
International Preliminary Report on Patentability from international application No. PCT/US2011/022729, dated Aug. 9, 2012, 13 pages.

\* cited by examiner

IMPLANTABLE MEDICAL DEVICE BATTERY

TECHNICAL FIELD

This disclosure relates to batteries for use with implantable medical devices.

BACKGROUND

As implantable medical device (IMD) technology advances in an attempt to address a myriad of life sustaining/enhancing needs, issues such as IMD battery longevity, IMD size and shape, IMD mass, and patient comfort remain key considerations in the IMD design process. Much attention is typically placed on the power source of an implantable medical device during the IMD design process. Battery size and capacity, for example, significantly impact the physical configuration of the IMD and the duration of service time within the patient before battery replacement or recharge is required.

A conventional approach to providing power within an implantable medical device involves the use of a self-contained battery, not unlike a common battery which is commercially available to the consumer. Such a self-contained battery includes active electrochemical cell components housed in a battery can. Battery housing connectors or contacts are provided for establishing electrical connections to circuitry disposed within the implantable medical device.

The battery component of an IMD requires the allocation of an appreciable percentage of usable space within the IMD. For this reason, reducing the size of an IMD battery is a desirable design objective. However, reducing IMD battery size results in a corresponding reduction in battery capacity, which necessarily places limits on the ability to make significant battery size reductions using conventional IMD battery design principles.

Moreover, the can of a conventional IMD battery may create "dead space" within the implantable medical device (e.g., a can having a substantially square or rectangular shape). Although a thoughtful design approach can help to reduce the amount of such dead space, an appreciable volume of space within the IMD typically remains unusable when employing a conventional IMD battery.

SUMMARY

The disclosure includes a tubular battery for an IMD. The tubular battery is configured to mate coaxially with an electronic component subassembly of an IMD. The tubular battery includes a biocompatible tubular battery housing. An external surface of the battery housing also functions as a portion of the external surface of an assembled IMD. A battery header including a feedthrough is sealed to an open end of the battery housing. The feedthrough forms an electrical connection with an electronic component subassembly of an IMD that is coaxially mated with the tubular battery. The IMD also includes a tubular cover sealed to the battery header opposite the tubular battery housing to form an enclosure encasing the feedthrough and the electronic component subassembly. The tubular battery housing and the tubular cover may combine to form the external housing and provide shielding for an assembled IMD.

In different examples, the tubular battery may be a component of a cardiac rhythm management therapy delivery device, an implantable neurostimulator, an implantable leadless stimulator such as a microstimulator, a pressure sensor, an implantable drug delivery pump or other IMD. The same tubular battery configuration may be suitable for different IMD configurations.

In one aspect, the disclosure is directed to a battery comprises a tubular housing. An external surface of the tubular housing comprises a biocompatible material. The battery further comprises a battery header secured to an open end of the tubular housing, and the tubular housing and the battery header combine to form a substantially sealed enclosure. The battery also comprises one or more voltaic cells within the substantially sealed enclosure, and a feedthrough electrically connected to the voltaic cells and extending through the battery header to form a battery terminal. The battery header includes a radial groove opposite the tubular housing, and the radial groove is configured to receive a mating snap-fit electronic component subassembly of an implantable medical device.

In another aspect, the disclosure is directed to an implantable medical device comprising a battery, the battery including: a tubular battery housing, wherein an external surface of the tubular battery housing comprises a biocompatible material, a battery header secured to an open end of the tubular battery housing, wherein the tubular battery housing and the battery header combine to form a substantially sealed enclosure, one or more voltaic cells within the substantially sealed enclosure, and a feedthrough electrically connected to the voltaic cells and extending through the battery header to form a battery terminal. The implantable medical device further comprising an electronic component subassembly, the electronic component subassembly including: an electronics tray secured to the battery header opposite the tubular battery housing, and a set of electronic components coupled to the electronics tray and electrically connected to the battery terminal. The implantable medical device further comprising a tubular cover secured to the battery header opposite to the tubular battery housing, wherein the battery header and the tubular cover combine to form an enclosure encasing the feedthrough and the electronic component subassembly.

In another aspect, the disclosure is directed to a method of manufacturing an implantable medical device comprising obtaining a battery, the battery including: a tubular battery housing, wherein an external surface of the tubular battery housing comprises a biocompatible material, a battery header secured to an open end of the tubular battery housing, wherein the tubular battery housing and the battery header combine to form a substantially sealed enclosure, one or more voltaic cells within the substantially sealed enclosure, and a feedthrough electrically connected to the voltaic cells and extending through the battery header to form a battery terminal. The method further comprises obtaining an electronic component subassembly, the electronic component subassembly including: an electronics tray and a set of electronic components coupled to the electronics tray and electrically connected to the battery terminal. The method further comprises securing the electronic tray to the battery header opposite the tubular battery housing; obtaining a tubular cover; and securing the tubular cover to the battery header opposite to the tubular battery housing to form an enclosure encasing the feedthrough and the electronic component subassembly.

The details of one or more examples of the disclosure are set forth in the accompanying drawings and the description below. Other features, objects, and advantages of the disclosure will be apparent from the description and drawings, and from the example statements provided below.

DETAILED DESCRIPTION

Figure 1:
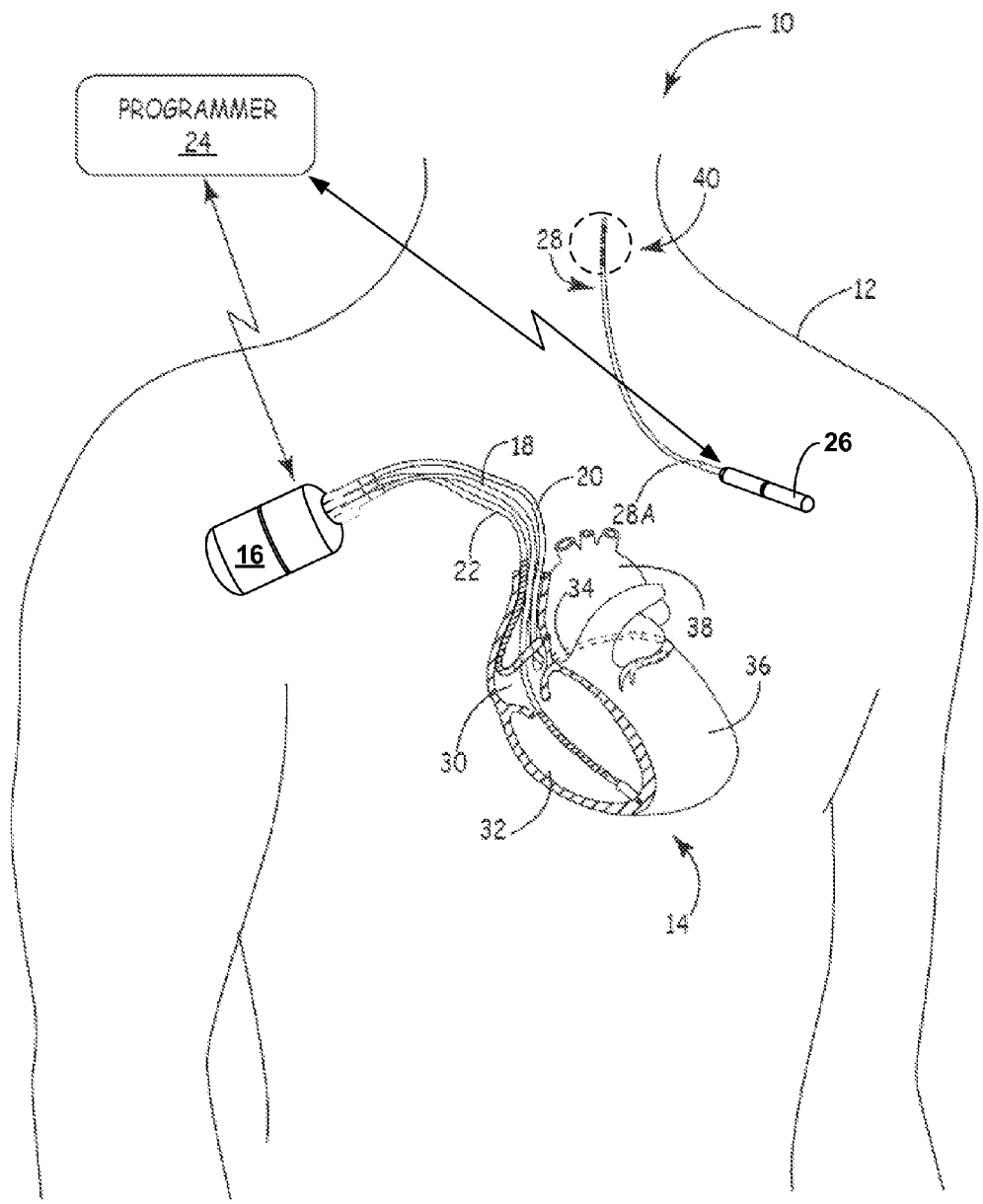
FIG. 1 is a conceptual diagram illustrating an example therapy system including an implantable cardiac device (ICD) and an implantable neurostimulator (INS).

FIG. 1 is a conceptual diagram illustrating an example system 10 that provides therapy to patient 12. Therapy system 10 includes implantable cardiac device (ICD) 16, which is connected to leads 18, 20, and 22, and programmer 24. ICD 16 may be, for example, a device that provides cardiac rhythm management therapy to heart 14, and may include, for example, an implantable pacemaker, cardioverter, and/or defibrillator that provide therapy to heart 14 of patient 12 via electrodes coupled to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation pulses.

In some examples, ICD 16 may not deliver cardiac rhythm management therapy to heart 14, but may instead only sense electrical cardiac signals of heart 14 and/or other physiological parameters of patient 12 (e.g., blood oxygen saturation, blood pressure, temperature, heart rate, respiratory rate, and the like), and store the electrical cardiac signals and/or other physiological parameters of patient 12 for later analysis by a clinician. In such examples, ICD 16 may be referred to as a patient monitoring device. Examples of patient monitoring devices include, but are not limited to, the Reveal Plus Insertable Loop Recorder, which is available from Medtronic, Inc. of Minneapolis, Minn. For ease of description, ICD 16 will be referred to herein as a cardiac rhythm management therapy delivery device.

Therapy system 10 further comprises implantable electrical stimulator 26, which is coupled to lead 28. Electrical stimulator 26 may also be referred to as an implantable neurostimulator (INS) 26. INS 26 may be any suitable implantable medical device (IMD) that includes a signal generator that generates electrical stimulation signals that may be delivered to a tissue site of patient 12, e.g., tissue within or proximate a brain, a vagus nerve, a spinal cord, cardiac fat pad, or heart 14 of patient 12.

In the example shown in FIG. 1, the components of ICD 16 and INS 26 are enclosed in separate housings, such that ICD 16 and INS 26 are physically separate devices. In other examples, the functionality of ICD 16 and INS 26 may be performed by an IMD that includes both a cardiac therapy module that generates and delivers at least one of pacing, cardioversion or defibrillation therapy to patient 12 and an electrical stimulation therapy module that generates and delivers electrical stimulation to a target tissue site within patient 12, which may be proximate a nerve or may be an extravascular tissue site that is not proximate a nerve. In other examples, a system may include only a single IMD that provides either ICD or INS functionality.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 may detect fibrillation employing one or more fibrillation detection techniques known in the art.

In the example of FIG. 1, INS 26 has been implanted in patient 12 proximate to an nonmyocardial target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26.

INS 26 may also be referred to as a signal generator. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation.

Delivery of electrical stimulation by INS 26 to one or more target tissues sites may provide cardioprotective benefits to patient 12. For example, delivery of electrical stimulation to a tissue site proximate a nerve of patient 12 may help treat heart failure. In addition, delivery of electrical stimulation to a tissue site proximate a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. Delivery of electrical stimulation by INS 26 may compliment antitachycardia therapy (e.g., antitachycardia pacing, cardioversion or defibrillation) by ICD 16 or provide back-up therapy to the cardiac rhythm therapy provided by ICD 16. For example, if ICD 16 is unavailable to provide therapy to patient 12, e.g., due to a low power level, INS 26 may deliver therapy to patient 12 to help terminate or prevent a cardiac event (e.g., tachycardia).

In some examples, INS 26 delivers electrical stimulation to peripheral nerves that innervate heart 14, or fat pads on heart 14 that may contain nerve bundles. In the example shown in FIG. 1, electrodes of lead 28 are positioned to deliver electrical stimulation to a vagus nerve (not shown) of patient 12. Although INS 26 is referred to throughout the remainder of the disclosure as a "neurostimulator" and as delivering neurostimulation pulses, in other examples, INS 26 may deliver electrical stimulation to any suitable nonmyocardial tissue site within patient 12, which may or may not be proximate a nerve or neural tissue.

In the example shown in FIG. 1, INS 26 provides electrical stimulation therapy of a parasympathetic nerve, such as a vagus nerve, of patient 12. Stimulation of a parasympathetic nerve of patient 12 may help slow intrinsic rhythms of heart 14, which may facilitate antitachyarrhythmia therapy (e.g., antitachycardia pacing, cardioversion or defibrillation) delivered by ICD 16. In this way, neurostimulation by INS 26 may help control a heart rate of patient 12 or otherwise control cardiac function.

In other examples, electrodes of lead 28 may be positioned to deliver electrical stimulation to any other suitable nerve, organ, muscle or muscle group in patient 12, which may be selected based on, for example, a therapy regimen selected for a particular patient. In some examples, INS 26 may deliver electrical stimulation to other parasympathetic nerves, baroreceptors, the carotid sinus or a cardiac branch of the vagal trunk of patient 12 in order to compliment the delivery of therapy by ICD 16.

The electrical stimulation signals generated and delivered by INS 26 may be referred to as neurostimulation signals. However, in some examples, INS 26 may deliver electrical stimulation to a target tissue site 40 that is not proximate to a nerve. For example, in some examples, INS 26 may deliver electrical stimulation to a peripheral nerve field site, whereby electrodes 124 (FIG. 5) are implanted in a region where patient 12 experiences pain. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 or an IMD generally delivers electrical stimulation to other tissue sites.

Figure 2:
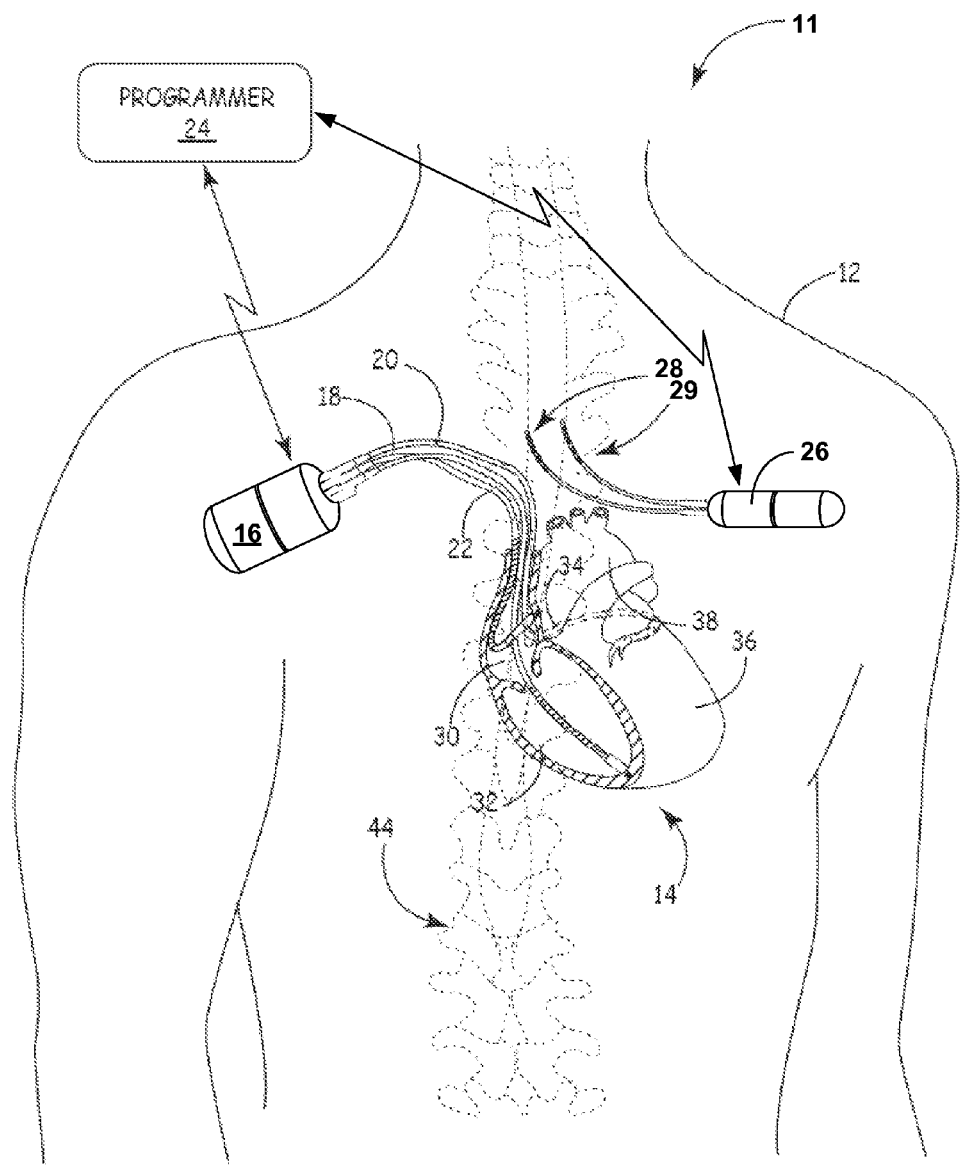
FIG. 2 is a conceptual diagram illustrating another example therapy system that includes the ICD and the INS.

As another example, as shown in FIG. 2, INS 26 may be positioned to deliver electrical stimulation to spinal cord 44 of patient 12. Stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation therapy, delivered by ICD 16. In this way, ICD 16 and INS 26 may operate in conjunction with each other to help prevent arrhythmias of heart 14 of patient 12, as well as to terminate detected arrhythmias.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 of patient 12, the neurostimulation may produce paresthesia, which may help reduce the discomfort felt by patient 12 from the delivery of stimulation by ICD 16.

In the example shown in FIG. 2, in therapy system 11, INS 26 is coupled to two leads 28, 29 to provide bilateral stimulation of spinal cord 44. Leads 28, 29 may be introduced into spinal cord 44 in the thoracic region, as shown in FIG. 2. In other examples, leads 28, 29 may be introduced into spinal cord 44 in the cervical or lumbar regions. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

Programmer 24 may include a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, heart sounds, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by ICD 16, such as cardioversion or pacing therapies. In some examples, the user may activate certain features of ICD 16 by entering a single command via programmer 24, such as depression of a single key or combination of keys of a keypad or a single point-and-select action with a pointing device.

The user may also use programmer 24 to retrieve information from INS 26 regarding the performance or integrity of INS 26 or leads 28, 29 (if INS 26 is connected to more than one lead) or a power source of INS 26. In addition, the user may use programmer 24 to program INS 26. For example, with the aid of programmer 24 or another computing device, a user may select values for therapy parameters for controlling therapy delivery by INS 26.

Programmer 24 may communicate with ICD 16 and INS 26 via wireless communication using any techniques known in the art. Examples of communication techniques may include, for example, low frequency or RF telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

The configurations of therapy system 10 illustrated in FIGS. 1-2 are merely examples. In other examples, a therapy system may include epicardial leads and/or patch electrodes instead of or in addition to the transvenous leads 18, 20, 22 illustrated in FIG. 1.

In other examples of therapy systems that provide electrical stimulation therapy to heart 14, a therapy system may include any suitable number of leads coupled to ICD 16, and each of the leads may extend to any location within or proximate to heart 14. Other examples of therapy systems may include three transvenous leads located as illustrated in FIGS. 1-2, and an additional lead located within or proximate to left atrium 38. Other examples of therapy systems may include a single lead that extends from ICD 16 into right atrium 30 or right ventricle 32, or two leads that extend into a respective one of the right ventricle 32 and right atrium 30.

Figure 3:
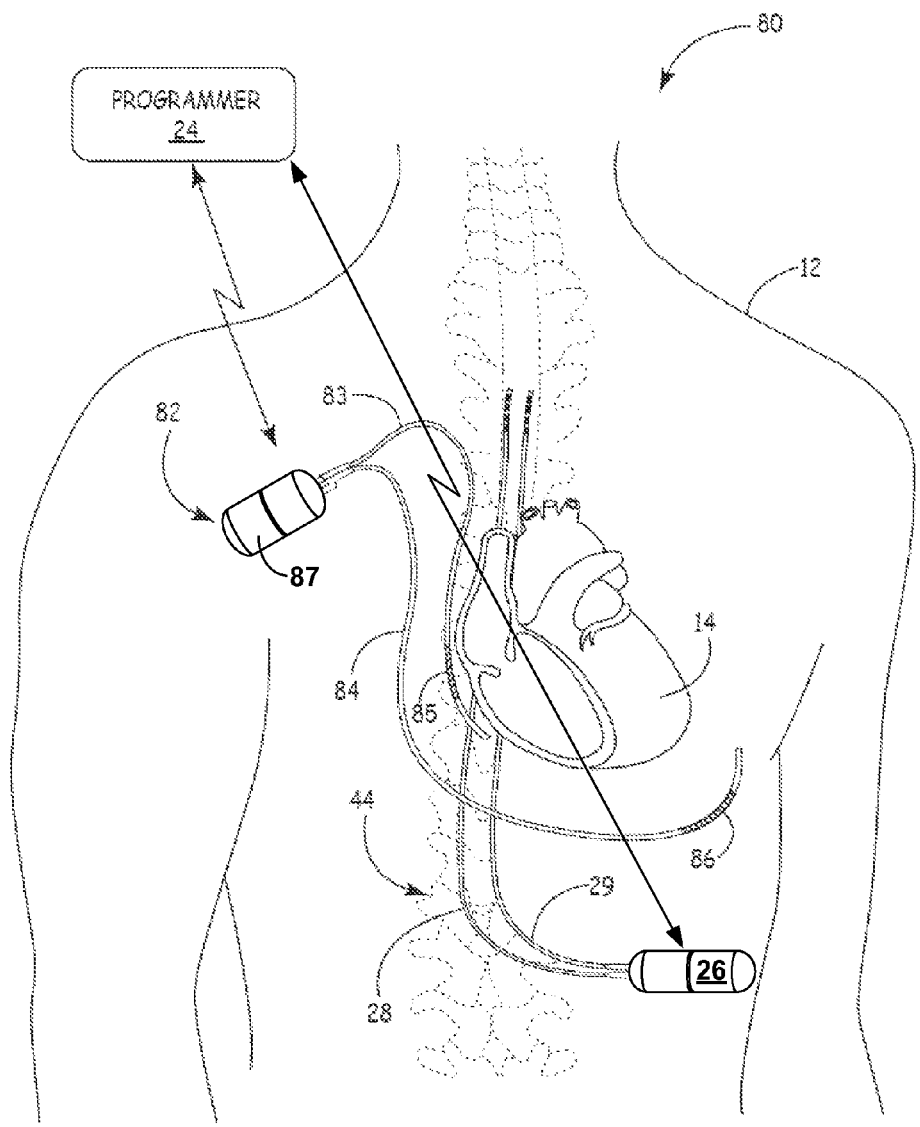
FIG. 3 is a conceptual diagram illustrating another example therapy system that includes an ICD and an INS.

FIG. 3 is a conceptual diagram of another example therapy system 80 that includes two medical devices to provide therapy to patient 12. In addition to INS 26, therapy system 80 includes ICD 82, which delivers electrical stimulation to heart 14 without intravascular leads. ICD 82 is coupled to extravascular leads 83, 84, which each include at least one electrode 85, 86, respectively. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, or any other type of extrathoracic electrode, such as a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart.

Leads 83, 84 may be electrically coupled to stimulation modules, and, in some cases, sensing modules, that are enclosed within housing 87 of ICD 82. As with housing 70 of ICD 16 (FIG. 1), housing 87 may comprise a hermetic housing that substantially encloses the components of ICD 16, such as a sensing module, stimulation generator, processor and the like. Components of an example ICD 16 or ICD 82 are described with respect to FIG. 4. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87 (or an electrode attached to an outer surface of housing 87), or between electrode 86 and housing 87, e.g., in a unipolar configuration.

Just as with ICD 16 (FIG. 1) that delivers stimulation to heart 14 via intravascular electrodes, the delivery of electrical stimulation by INS 26 may interfere with the ability of ICD 82 to sense cardiac signals and deliver appropriate therapy upon the detection of an arrhythmia. ICD 82 may include a sensing module similar to that of ICD 16. In some cases, the sensing module may sense the electrical stimulation delivered by INS 26 and mischaracterize the signals as cardiac signals, which may cause ICD 82 to deliver inappropriate therapy to heart 14 of patient 12.

While the disclosure primarily refers to therapy system 10 including ICD 16 (FIG. 1) and INS 26, the description of the techniques, systems, and devices herein are also applicable to therapy system 80 including ICD 82 and INS 26. In addition, a system may include one or more IMDs including tubular batteries. The IMDs may or more not be coupled to leads, e.g., one or more IMDs may include housing electrodes instead of electrode disposed on a lead. As another example, one or more IMDs could include a pump in addition to or alternatively to electrodes.

Figure 4:
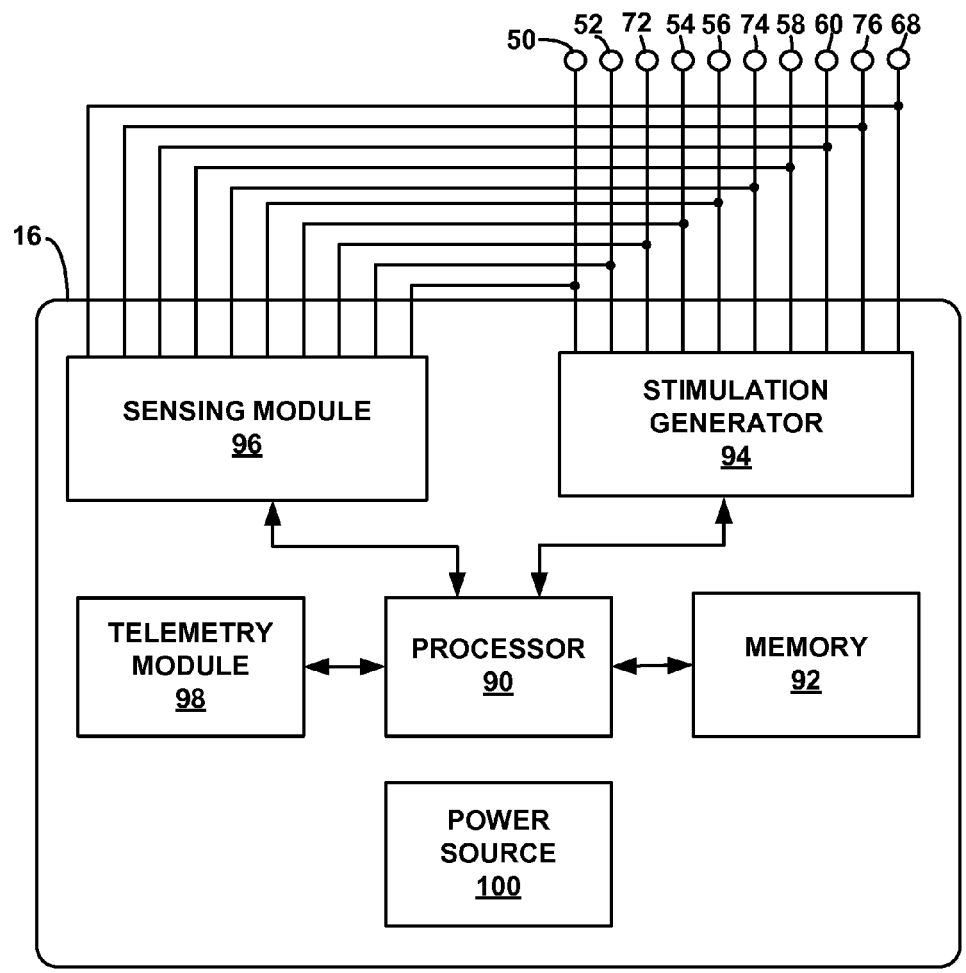
FIG. 4 is a functional block diagram of an example ICD that generates and delivers electrical stimulation to a heart of a patient.
Figure 7:
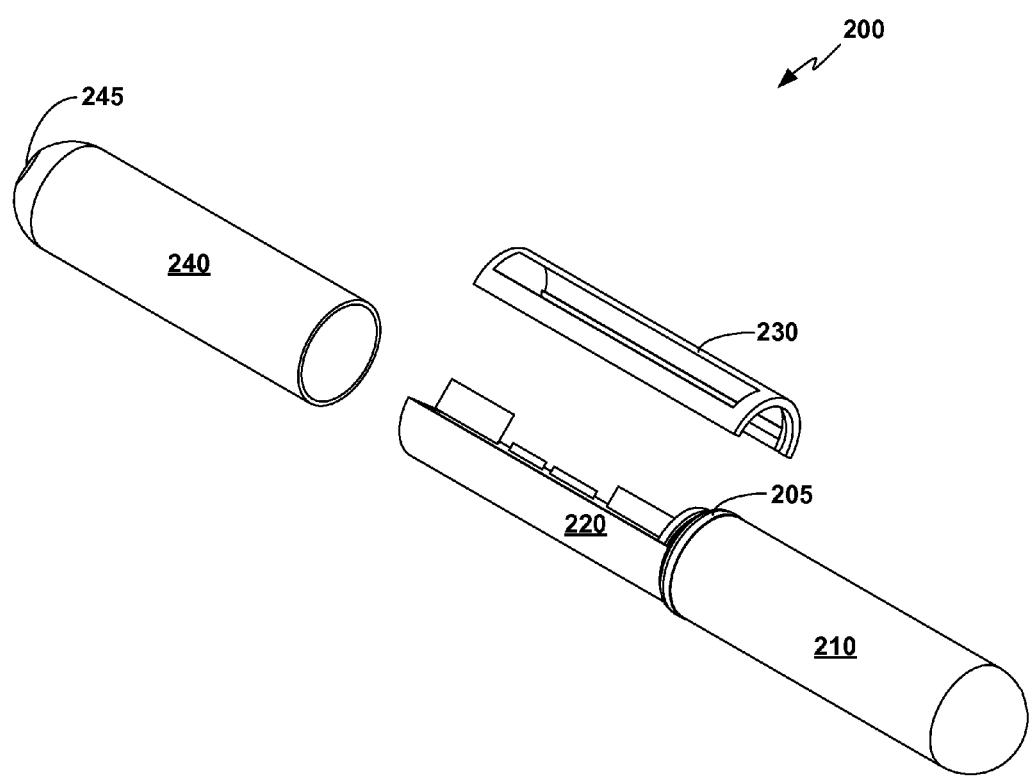
FIG. 7 is an exploded view of an example IMD including a tubular battery.

FIG. 4 is a functional block diagram of an example configuration of ICD 16 (FIG. 1), which includes processor 90, memory 92, stimulation generator 94, sensing module 96, telemetry module 98, and power source 100. The block diagram shown in FIG. 4 may also illustrate an example configuration of ICD 82 (FIG. 3) and IMD 200 (FIG. 7). Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls stimulation generator 94 to deliver stimulation therapy to heart 14 according to a selected one or more of therapy programs, which may be stored in memory 92. Specifically, processor 44 may control stimulation generator 94 to deliver electrical pulses with the amplitudes, pulse widths, frequency, or electrode polarities specified by the selected one or more therapy programs.

Stimulation generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Stimulation generator 94 is configured to generate and deliver electrical stimulation therapy to heart 14 to manage a rhythm of heart 14. For example, stimulation generator 94 may deliver defibrillation shocks to heart 14 via at least two electrodes 68, 72, 74, 76. Stimulation generator 94 may deliver pacing pulses via ring electrodes 50, 54, 58 coupled to leads 18, 20, and 22, respectively, helical electrodes 52, 56, and 60 of leads 18, 20, and 22, respectively, and/or housing electrode 68. In some examples, stimulation generator 94 delivers pacing, cardioversion or defibrillation therapy in the form of electrical pulses. In other examples, stimulation generator 94 may deliver one or more of these types of therapy in the form of other signals, such as sine waves, square waves, or other substantially continuous time signals.

In some examples, stimulation generator 94 may include a switch module (not shown in FIG. 4) and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, stimulation generator 94 may independently deliver stimulation to electrodes 50, 52, 54, 56, 58, 60, 68, 72, 74, and 76 or selectively sense via one or more of electrodes 50, 52, 54, 56, 58, 60, 68, 72, 74, and 76 without a switch matrix.

Sensing module 96 monitors signals from at least one of electrodes 50, 52, 54, 56, 58, 60, 68, 72, 74, and 76 in order to monitor electrical activity of heart 14, e.g., via an EGM signal. Sensing module 96 may also include a switch module (not shown in FIG. 4) to select a particular subset of available electrodes to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of sensing module 96 may couple the outputs from the selected electrodes to one of the sensing channels.

In some examples, sensing module 96 may include a plurality of channels. One channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 96, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, in one operating mode of sensing module 96, the P-wave amplifier may take the form of an automatic gain controlled amplifier that provides an adjustable sensing threshold as a function of the measured P-wave amplitude of the heart rhythm. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an EGM. In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When a pacing code includes "D" as the third letter in the code, it may indicate that the sensed signal is used for tracking purposes.

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Stimulation generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by stimulation generator 94, and thereby control the basic timing of cardiac pacing functions, including anti-tachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response. A portion of memory 92 may be configured as a plurality of recirculating buffers, capable of holding series of measured intervals, which may be analyzed by processor 90 to, for example, determine whether heart 14 of patient 12 is presently exhibiting atrial or ventricular tachyarrhythmia.

In some examples, an arrhythmia detection method may include any suitable tachyarrhythmia detection algorithms. In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by stimulation generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of stimulation generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion pulse by stimulation generator 94 is controlled by the cardioversion/defibrillation control module of processor 90. Following delivery of the fibrillation or tachycardia therapy, processor 90 may return stimulation generator 94 to a cardiac pacing function and await the next successive interrupt due to pacing or the occurrence of a sensed atrial or ventricular depolarization.

Stimulation generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 94.

Telemetry module 98 includes any suitable hardware, firmware, software or any combination thereof for communicating with another device, such as INS 26 or programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer.

In some examples, processor 90 may transmit atrial and ventricular heart signals (e.g., ECG signals) produced by atrial and ventricular sense amp circuits within sensing module 96 to programmer 24. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis. Examples of a rechargeable battery include, but are not limited to, a lithium ion battery, a lithium/silver vanadium oxide battery, a lithium polymer battery or a supercapacitor. As one example, power source 100 may be battery 210, as shown in FIG. 7.

In some examples, data from sensing module 96 may be uploaded to a remote server, from which a clinician or another user may access the data to determine whether a potential sensing integrity issue exists. An example of a remote server includes the CareLink Network, available from Medtronic, Inc. of Minneapolis, Minn.

Figure 5:
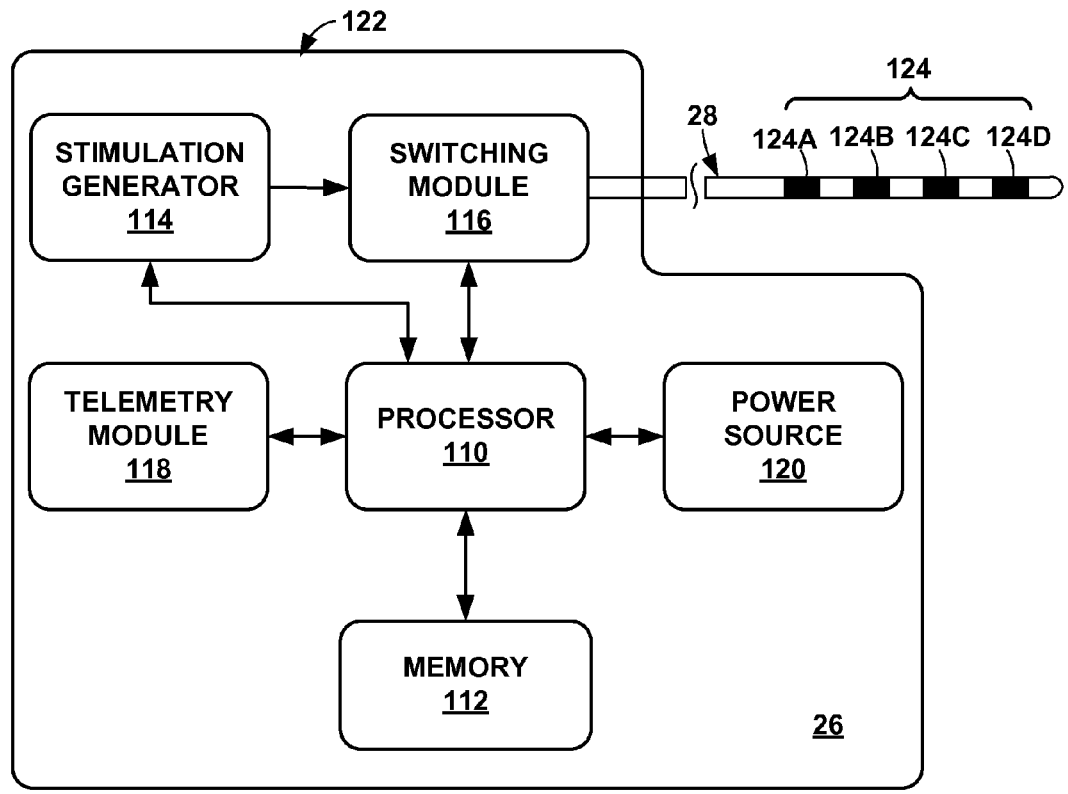
FIG. 5 is a functional block diagram of an example INS that generates and delivers electrical stimulation signals to a tissue site within the patient.

Telemetry module 98 may also be useful for communicating with INS 26, which may also include a telemetry module as described with respect to FIG. 5. In some examples, INS 26 and ICD 16 may communicate with each other by way of RF communication techniques supported by the respective telemetry modules.

FIG. 5 is a functional block diagram of an example INS 26. INS 26 includes processor 110, memory 112, stimulation generator 114, switching module 116, telemetry module 118, and power source 120. The block diagram shown in FIG. 4 may also illustrate an example configuration of IMD 200 (FIG. 7). In the example shown in FIG. 5, processor 110, memory 112, stimulation generator 114, switching module 116, telemetry module 118, and power source 120 are enclosed within housing 122, which may be, for example a hermetic housing. As shown in FIG. 5, stimulation generator 114 is coupled to lead 28 either directly or indirectly (e.g., via a lead extension). Alternatively, stimulation generator 114 may be coupled to more than one lead directly or indirectly (e.g., via a lead extension, such as a bifurcating lead extension that may electrically and mechanically couple to two leads) as needed to provide neurostimulation therapy to patient 12.

In the example illustrated in FIG. 5, lead 28 includes electrodes 124A-124D (collectively referred to as "electrodes 124"). Electrodes 124 may comprise ring electrodes. In other examples, electrodes 124 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 5 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124.

Memory 112 includes computer-readable instructions that, when executed by processor 110, cause INS 26 to perform various functions. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring the impedance of electrodes 124.

Stimulation generator 114 generates stimulation signals, which may be pulses as primarily described herein, or continuous signals, such as sine waves, for delivery to patient 12 via selected combinations of electrodes 124. Processor 110 controls stimulation generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Processor 110 may also control switching module 116 to apply the stimulation signals generated by stimulation generator 114 to selected combinations of electrodes 124. In particular, switching module 116 couples stimulation signals to selected conductors within lead 28 which, in turn, deliver the stimulation signals across selected electrodes 124. Switching module 116 may be a switch array, switch matrix, multiplexer, or any other type of switching device suitable to selectively couple stimulation energy to selected electrodes. Hence, stimulation generator 114 is coupled to electrodes 124 via switching module 116 and conductors within lead 28. In some examples, INS 26 does not include switching module 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching module 116 may be configured to deliver multiple channels on a time-interleaved basis. In this case, switching module 116 serves to time division multiplex the output of stimulation generator 114 across different electrode combinations at different times to deliver multiple programs or channels of stimulation energy to patient 12.

Telemetry module 118 supports wireless communication between INS 26 and an external programmer 24 (FIG. 1) or another computing device, and, in some examples, between INS 26 and ICD 16 under the control of processor 110. Processor 110 of INS 26 may receive, as updates to programs, values for various stimulation parameters such as amplitude and electrode combination, from programmer 24 via telemetry module 118. The updates to the therapy programs may be stored within memory 112.

The various components of INS 26 are coupled to power source 120, which may include a rechargeable or non-rechargeable battery. A non-rechargeable battery may be selected to last for several years, while a rechargeable battery may be inductively charged from an external device, e.g., on a daily or weekly basis. In other examples, power source 120 may be powered by proximal inductive interaction with an external power source carried by patient 12. As one example, power source 120 may be battery 210, as shown in FIG. 7.

Figure 6:
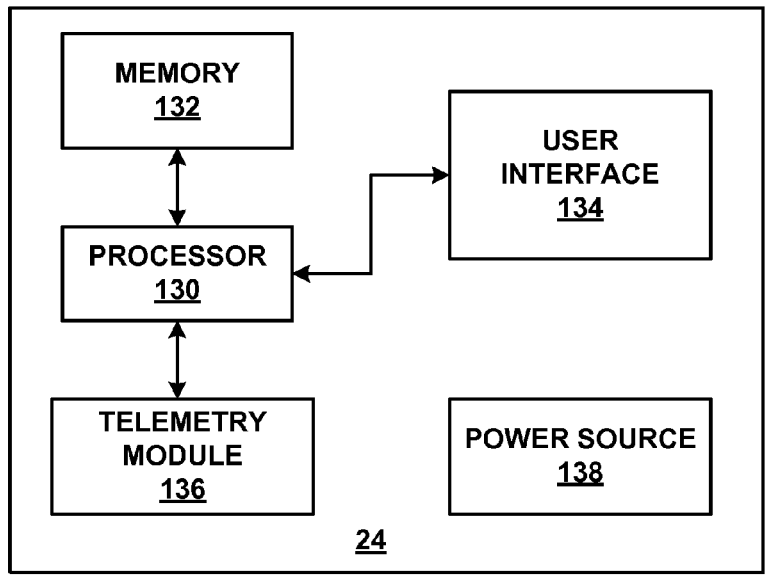
FIG. 6 is a functional block diagram of an example medical device programmer.

FIG. 6 is block diagram of an example programmer 24. As shown in FIG. 4, programmer 24 includes processor 130, memory 132, user interface 134, telemetry module 136, and power source 138. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 (FIG. 1), INS 26 (FIG. 1) or IMD 200 (FIG. 7). The clinician may interact with programmer 24 via user interface 134, which may include display to present graphical user interface to a user, and a keypad or another mechanism for receiving input from a user.

Processor 130 can take the form one or more microprocessors, DSPs, ASICs, FPGAs, programmable logic circuitry, or the like, and the functions attributed to processor 102 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed over heart 14, as described above with reference to FIG. 1. Telemetry module 136 may be similar to telemetry module 98 of ICD 16 (FIG. 4) or telemetry module 118 of INS 26 (FIG. 5).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

FIG. 7 is an exploded view of IMD 200. IMD 200 includes a tubular battery 210 that is coaxially mated with electronic component subassembly 220 of IMD 200. FIGS. 8A-8E illustrate steps for assembling IMD 200. Because FIGS. 8A-8E more clearly illustrate some details of IMD 200 than FIG. 7, IMD 200 is described in reference to FIGS. 8A-8E as well as FIG. 7. As is clear from the following examples, IMD 200 may configured for use as ICD 16, ICD 82, or as IND 26 in therapy systems 10, 11, 80 (FIGS. 1, 2 respectively). In this manner, the functionalities of ICD 16, ICD 82 and IND 26 are also attributable to specific configurations of IMD 200.

In different examples, IMD 200 can be an ICD that delivers a cardiac rhythm management therapy, an INS that delivers deliver electrical stimulation therapy to a nerve or other tissue of a patient, an implantable drug pump that delivers a drug therapy, an implantable sensor, such a sensor that senses one or more physiological parameters of a patient via one or more electrodes or other sensors, such as a pressure sensor that measure pressure within a patient cavity, an IMD that delivers a different medical therapy, or any combination of two or more thereof. In some examples, IMD 200 may include electrodes on or protruding through its exterior surface, e.g., tubular cover 240, for delivering electrical stimulation and/or sensing physiological parameters of the patient; in such a configuration IMD 200 may be considered a microstimulator. IMD 200 may also connect to one or more medical leads for delivering electrical stimulation and/or sensing physiological parameters of the patient. IMD 200 is shown with an exemplary port 245, which may be, depending on the configuration of IMD 200, provide a connector to receive a medical lead or a drug delivery outlet to receive a catheter or deliver a drug to a patient. In other examples, IMD 200 may have several ports 245 to accommodate more than one lead or catheter.

As these examples illustrate, tubular battery 210 can be a component in a wide variety of IMD configurations. Depending on its functionality, IMD 200 may be suitable for implantation at any number of locations within a patient as required to provide for the designed functionality of IMD 200. As some examples, IMD 200 may be implanted intravascularly, transvascularly, adjacent cardiac tissues, nerves and/or other locations of a patient as necessary.

In some examples, more than one IMD 200, having common or different configurations, may be implanted within a patient to provide desired patient therapies and/or sensing. For example, an IMD 200 may be configured as a microstimulator. In some examples, one or more other IMDs 200 may be used simultaneously to provide cardiac rhythm management therapy to a patient. For example each microstimulator may perform only part of cardiac rhythm management therapy, and a plurality of microstimulators may work in unison to provide cardiac rhythm management therapy to a patient. Such microstimulators may communicate using RF telemetry, by other suitable techniques, or the cardiac rhythm management therapy delivered by a plurality of microstimulators may be coordinated by an external device such as programmer 24. Likewise, a plurality of IMDs 200 may be used simultaneously to provide neurostimulation therapy to a patient.

Tubular battery 210 includes biocompatible tubular battery housing 212 and battery header 205. Battery header 205 is secured to an open end of tubular battery housing 212. Tubular battery housing 212 and battery header 205 combine to form a substantially sealed enclosure encasing voltaic cells 204. As an example, voltaic cells 204 may comprise lithium/silver vanadium oxide voltaic cells. Battery header 205 includes feedthrough 218, which is electrically connected to voltaic cells 204 and extends through battery header 205 to form the positive battery terminal of battery 210. Feedthrough 218 is electrically isolated from battery header 205 by insulator 219. Battery header 205 and tubular battery housing 212 comprise metallic alloys and provide the ground or negative terminal of tubular battery 210. For example, battery header 205 and tubular battery housing 212 may be a deep drawn component formed from a stainless steel or titanium alloy. In other examples, tubular battery 210 may include a separate feedthrough or ground contact on battery header 205 for the negative terminal.

Tubular battery 210 has a length greater than its diameter. As examples, the length of tubular battery 210 may be between about 1.1-10 times the diameter of tubular battery 210. As an example, the length of IMD 200 may be about 46.5 millimeters (mm) and the diameter of tubular battery 210 and IMD 200 may be about 6.1 mm.

Figure 8A:
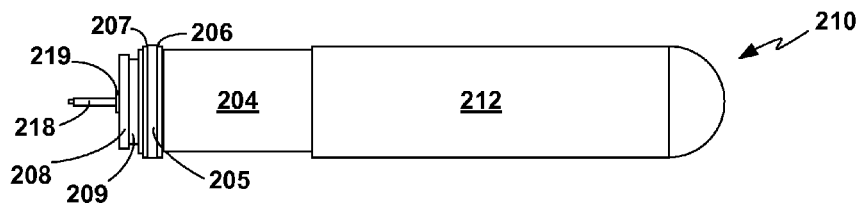
FIGS. 8A-8E illustrate steps for assembling the IMD shown in FIG. 7.
Figure 8B:
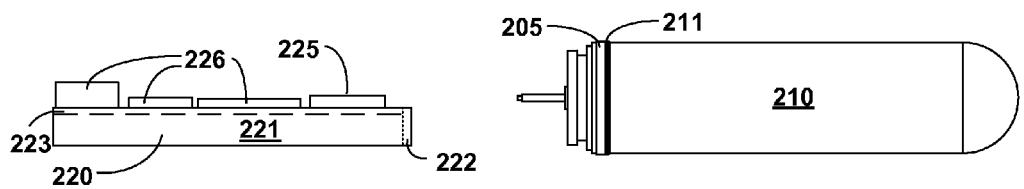

Battery header 205 is generally circular and matches the circular cross section of tubular battery housing 212. As best shown in FIG. 8A, battery header 205 includes features that facilitate the assembly of IMD 200. For example, battery header 205 includes notch 206, which is located on the perimeter of battery header 205 adjacent to tubular battery housing 212. As an example, the outer diameter of battery header 205 may be about equal to the outer diameter of tubular battery housing 212, and the outer diameter of battery header 205 at notch 206 may be about equal to the inner diameter of tubular battery housing 212. In this manner, battery header 205 fits within the open end of tubular battery housing 212. As shown in FIG. 8B, battery header 205 may be hermetically sealed to the open end of tubular battery housing 212 with weld joint 211.

Battery header 205 also includes radial groove 209 opposite tubular housing 212. Radial groove 209 is configured to receive electronic component subassembly 220. Specifically, electronic component subassembly 220 includes inner radial protrusion 222 that fits within radial groove 209 such that electronic component subassembly 220 is secured to battery header 205 with a snap-fit. In other examples, electronic component subassembly 220 may be secured to battery header 205 using other techniques such as welding. The snap-fit interface of electronic component subassembly 220 and battery header 205 further includes outer radial protrusion 208 on battery header 205. Outer radial protrusion 208 is configured to mate with the inner diameter of tray 221 of electronic component subassembly 220.

Whereas tubular battery 210 provides the power for IMD 200, electronic component subassembly 220 provides and/or controls the medical therapy and/or sensing functions of IMD 200. Electronic component subassembly 220 includes tray 221. As previously mentioned, tray 221 includes inner radial protrusion 222 which mates with radial groove 209 of battery header 205. Circuit board 223 is mounted within tray 221. As an example, circuit board 223 may be a printed circuit board (PCB) or a flexible circuit board. Tray 221 may comprise an insulative material, such as plastic, to electrically isolate circuit board 223, electrical contact 225 and electronic components 226 from battery header 205 and tubular cover 240. In one example, tray 221 comprises a suitable electrical insulating biocompatible polymer material, such as a polypropylene material.

Electronic components 226 and electrical contact 225 are located on circuit board 223. Spot weld 229 forms an electrical connection between electrical contact 225 and feedthrough 218. Circuit board 223 and electronic components 226 may connect to the negative or ground battery terminal of tubular battery 210 via one or more ground contacts with tubular cover 240 and/or battery header 205 (ground contacts not shown). Electronic components 226 may include, e.g., a programmable processor configured to control delivery of a medical therapy to a patient by IMD 200 and/or sense one or more physiological parameters of the patient with IMD 200, memory, a coil for telemetry and/or inductive power, a telemetry module (e.g., transmitter and/or receiver), a pump for delivering drug therapy to a patient, a stimulation generator for delivering simulation therapy such as cardiac stimulation and/or neurostimulation. As an example, if electronic component subassembly 220 includes a pump for delivering drug therapy to a patient, electronic component subassembly 220 may also include a fluid reservoir (not shown) containing the drug. As these examples illustrate, the configuration of electronic component subassembly 220 and electronic components 226 determines the functionality of IMD 200.

IMD 200 further includes insulative shield 230 which, like tray 221 functions to separate circuit board 223, electrical contact 225 and electronic components 226 from tubular cover 240. For example, insulative shield 230 may comprise an insulative material, such as plastic, to electrically isolate board 223, electrical contact 225 and electronic components 226 from tubular cover 240. In one example, insulative shield 230 comprises a polypropylene material. Insulative shield 230 includes inner radial protrusion 232 which mates with radial groove 209 of battery header 205. Insulative shield 230 mates to battery header 205 opposite electronics tray 221 such that insulative shield 230 and electronics tray 230 substantially surround electronic components 226.

During assembly of IMD 200, tubular battery 210 is mated to electronic component subassembly 220 and then tubular cover 240 is sealed to battery header 205 opposite tubular battery housing 212 to form an enclosure encasing feedthrough 218 and the electronic component subassembly 220. Battery header 205 includes notch 207, which located on the perimeter of battery header 205 adjacent to tubular cover 240. As an example, the outer diameter of battery header 205 may be about equal to the outer diameter of tubular cover 240, and the outer diameter of battery header 205 at notch 207 may be about equal to the inner diameter of tubular cover 240. In this manner, battery header 205 fits within the open end of tubular cover 240. As shown in FIG. 8E, battery header 205 may be hermetically sealed to the open end of tubular cover 240 with weld joint 241 to form a hermetically sealed enclosure encasing electronic component subassembly 220. Tubular cover 240 may comprise a biocompatible metallic alloy. For example, tubular cover 240 may be formed from a stainless steel or titanium alloy. As an example, tubular cover 240 may comprise a deep drawn component. As another example, tubular cover 240 may comprise machined component.

Tubular battery housing 212 and tubular cover 240 combine to form the external housing of IMD 200 and provide shielding for electronic components of IMD 200. In particular, as mentioned previously, battery housing 212 provides the negative or ground battery terminal of tubular battery 210. Tubular cover 240 is electrically connected to battery housing 212 via battery header 205 such that tubular battery housing 212 and tubular cover 240 combine to provide shielding for IMD 200. In this configuration electronic component subassembly 220 forms an electrical connection with either tubular cover 240 or battery header 212. For example, electronic component subassembly 220 may include a spring loaded contact that touches an interior surface of tubular cover 240. In other examples, tubular battery 210 may include a separate feedthrough or ground contact in battery header 205 for the negative terminal.

While IMD 200 including tubular battery 210 is shown and described as having a generally cylindrical shape with a generally circular cross, an IMD including a tubular battery can have different cross-sectional shapes within the spirit of this disclosure. For example, suitable cross-sectional shapes for an IMD including a tubular battery include but are not limited to circular, rectangular, triangular, square, hexagonal and octagonal shapes. As referred to herein, the term tubular does not indicate to any particular cross-sectional shape, but only indicates a component including a hollow elongated body.

The configuration of IMD 200, including tubular battery 210 may provide one or more advantages. For example, because electronic component subassembly 220 is secured directly to battery header 205 of tubular battery 210, electronic component subassembly 220 and tubular battery 210 may be considered a single structural component. For this reason, relatively low stress is placed on weld 229 even when IMD 200 is subjected to compressive or bending loads. In other examples, electronic component subassembly 220 and tubular battery 210 may connect with a flexible electrical interconnect, and the relative stability of electronic component subassembly 220 and tubular battery 210 will limit flexure failure fatigue of the electrical interconnect. Thus, IMD 200 facilitates a reliable electrical connection between electronic component subassembly 220 and tubular battery 210.

In addition, the configuration of IMD 200 may provide reliable hermetic sealing of IMD 200. In particular, the configuration of IMD 200 including tubular battery 210, electronic component subassembly 220 and tubular cover 240 does not require epoxy bonding during the assembly process of tubular battery 210, electronic component subassembly 220 and tubular cover 240. Imprecise epoxy bonding can adversely affect the integrity of hermetic sealing, such as the hermetic sealing provided by weld joints 211 and 241.

As another example, the configuration of IMD 200 including tubular battery 210, electronic component subassembly 220 and tubular cover 240 can provide low manufacturing costs. For example, tubular battery 210, electronic component subassembly 220 and tubular cover 240 can be separately manufactured and then assembled without epoxy or other adhesive. Therefore, the assembly process for IMD 200 does not require curing time for an epoxy or other adhesive and the functionality of tubular battery 210, electronic component subassembly 220 and tubular cover 240 can be evaluated prior to the final assembly of IMD 200.

FIGS. 8A-8E illustrate steps for assembling IMD 200. FIG. 8A illustrates assembly of tubular battery 210. In particular, voltaic cells 204 are positioned within tubular battery housing 212 and battery header 205 is secured to an open end of the tubular battery housing with weld join 211 (FIG. 8B). Tubular battery housing 212 and battery header 205 combine to form a substantially sealed enclosure encasing voltaic cells 204. Exemplary techniques for suitable for manufacturing a tubular battery such as tubular battery 210 are disclosed in commonly-assigned U.S. patent application Ser. No. 12/547,875, titled "IMPLANTABLE MEDICAL DEVICE WITH EXPOSED GENERATOR," filed on Aug. 26, 2009, the entire content of which is incorporated by reference herein.

Following the assembly of tubular battery 210, as shown in FIG. 8B, electronic component subassembly 220 is secured to battery header 205 opposite tubular battery housing 212. In particular, tray 221 of electronic component subassembly 220 is snap-fit to battery header 205. In other examples, electronic component subassembly 220 may be secured to battery header 205 using other techniques such as welding or a combination of techniques such as snap-fit and welding. Then, spot weld 229 (FIG. 8C) is added to form an electrical connection between electrical contact 225 of electronic component subassembly 220 and feedthrough 218 through battery header 205.

Figure 8C:
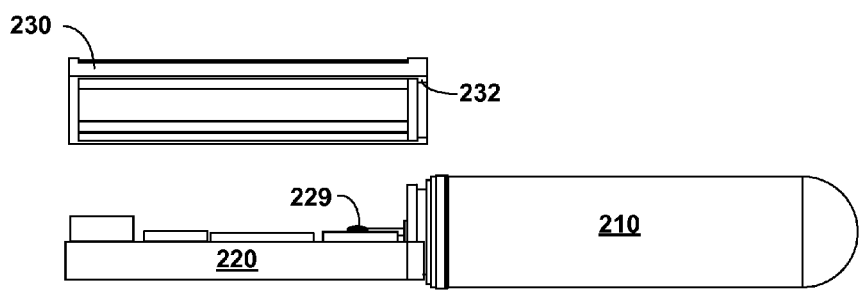

Next, as shown in FIG. 8C, insulative shield 230 is positioned over electronic component subassembly 220. In particular, insulative shield is snap-fit to battery header 205 opposite electronics tray 221 such that insulative shield 230 and electronics tray 230 substantially surround electronic components 226.

Figure 8D:
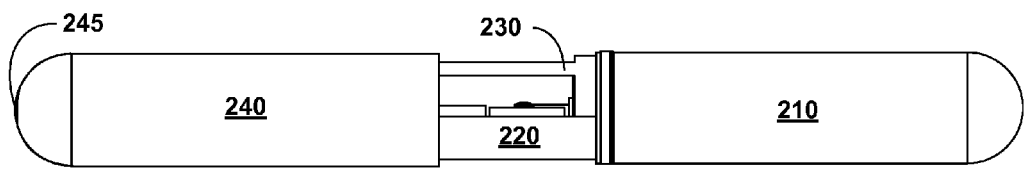
Figure 8E:
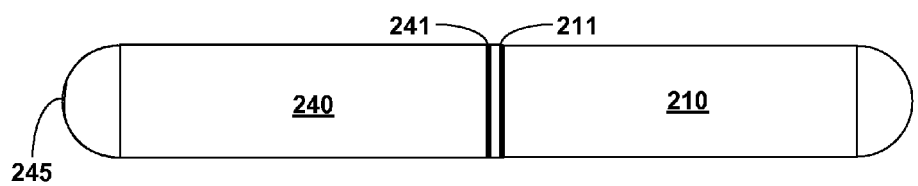

Once electronic component subassembly 220 and insulative shield 230 are in place, tubular cover 240 is positioned over insulative shield 230 and electronic component subassembly 220, as shown in FIG. 8D. In addition, as shown in FIG. 8E, battery header 205 is hermetically sealed to the open end of tubular cover 240 with weld joint 241.

The techniques described in this disclosure, including those attributed to ICD 16, INS 26, IMD 200, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 90 of ICD 16, processor 110 of INS 26, and/or processor 130 of programmer 24, any one or more parts of the techniques described herein may be implemented by a processor of one of the devices 16, 26, IMD 200, programmer 24 or another computing device, alone or in combination with ICD 16, INS 26, IMD 200 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the invention have been described. These and other examples are within the scope of the following claims.

The invention claimed is:
1. An implantable medical device comprising:
   a battery including:
      a tubular battery housing, wherein an external surface of the tubular battery housing comprises a biocompatible material,
      a battery header secured to an open end of the tubular battery housing, wherein the tubular battery housing and the battery header combine to form a substantially sealed enclosure, one or more voltaic cells within the substantially sealed enclosure, and a feedthrough electrically connected to the voltaic cells and extending through the battery header to form a battery terminal;

an electronic component subassembly including:

an electronics tray secured to the battery header opposite the tubular battery housing, and a set of electronic components coupled to the electronics tray and electrically connected to the battery terminal; and a tubular cover secured to the battery header opposite to the tubular battery housing, wherein the battery header and the tubular cover combine to form an enclosure encasing the feedthrough and the electronic component subassembly, wherein the battery header includes a radial groove opposite the tubular battery housing, wherein the electronics tray includes a radial protrusion, and wherein the electronics tray is snap-fit to the battery header in that the radial protrusion of the electronics tray is mated to the radial groove of the battery header.

2. The implantable medical device of claim 1, further comprising an insulative shield separating the set of electronic components from the tubular cover, wherein the insulative shield is mated to the radial groove opposite the electronics tray, wherein the electronics tray comprises an insulative material that insulates the set of electronic components from the tubular cover, and wherein the insulative shield and the electronics tray substantially surround the set of electronic components.

3. The implantable medical device of claim 1, wherein the electronics tray comprises an insulative material that insulates the set of electronic components from the tubular cover.

4. The implantable medical device of claim 1, further comprising a first weld joint hermetically sealing a first interface between the battery header and the tubular battery housing and a second weld joint hermetically sealing a second interface between the battery header and the tubular cover.

5. The implantable medical device of claim 1, wherein the battery terminal is a positively-charged battery terminal, wherein voltaic cells are electrically connected to the tubular battery housing such that the tubular battery housing and the battery header comprise a negatively-charged battery terminal.

6. The implantable medical device of claim 1, wherein the tubular battery housing, the battery header and the tubular cover comprise titanium alloys.

7. The implantable medical device of claim 1, wherein the tubular battery housing and the tubular cover are cylindrical, wherein the tubular battery housing and the tubular cover are have about equal diameters.

8. The implantable medical device of claim 1, wherein the tubular cover is a deep drawn component.

9. The implantable medical device of claim 1, wherein the implantable medical device is configured to one or more of a group consisting of:

deliver a cardiac rhythm management therapy;

deliver electrical stimulation therapy via one or more leads coupled to the implantable medical device;

deliver electrical stimulation therapy via one or more electrodes integrated in the tubular cover;

deliver drug therapy to a patient;

sense one or more physiological parameters of the patient via one or more electrodes; and measure pressure within a patient cavity.

10. The implantable medical device of claim 1, wherein the set of electronic components includes a processor configured to control delivery of a medical therapy to a patient by the implantable medical device and/or sense one or more physiological parameters of the patient with the implantable medical device.

11. The implantable medical device of claim 1, wherein the implantable medical device is configured to deliver a cardiac rhythm management therapy.

12. The implantable medical device of claim 1, wherein the implantable medical device is configured to deliver electrical stimulation therapy via one or more leads coupled to the implantable medical device.

13. The implantable medical device of claim 1, wherein the implantable medical device is configured to deliver electrical stimulation therapy via one or more electrodes integrated in the tubular cover.

14. The implantable medical device of claim 1, wherein the implantable medical device is configured to deliver drug therapy to a patient.

15. The implantable medical device of claim 1, wherein the implantable medical device is configured to sense one or more physiological parameters of the patient via one or more electrodes.

16. The implantable medical device of claim 1, wherein the implantable medical device is configured to measure pressure within a patient cavity.

17. The implantable medical device of claim 1, wherein the battery terminal is a positively-charged battery terminal.

18. The implantable medical device of claim 1, further comprising a weld joint hermetically sealing an interface between the battery header and the tubular housing.

19. The implantable medical device of claim 1, wherein the voltaic cells include lithium/silver vanadium oxide voltaic cells.

20. The implantable medical device of claim 2, wherein the insulative material is an electrically insulative material.

* * * * *